United States Patent [19]

Powers et al.

[11] Patent Number: 4,954,519

[45] Date of Patent: Sep. 4, 1990

[54] ISOCOUMARINS WITH BASIC SUBSTITUENTS AS SERINE PROTEASES INHIBITORS, ANTICOAGULANTS AND ANTI-INFLAMMATORY AGENTS

[75] Inventors: James C. Powers, Atlanta; Chih-Min Kam, Roswell; Steven W. Oweida; David N. Ku, both of Decatur, all of Ga.

[73] Assignee: Georgia Tech Research Corporation, Atlanta, Ga.

[21] Appl. No.: 374,980

[22] Filed: Jul. 3, 1989

Related U.S. Application Data

[63] Continuation-in-part of Ser. No. 43,647, Apr. 28, 1987, Pat. No. 4,845,242.

[51] Int. Cl.$^5$ .............................................. A61K 31/40
[52] U.S. Cl. .................................... 514/456; 514/822
[58] Field of Search .............................. 514/456, 822

[56] References Cited

U.S. PATENT DOCUMENTS 2,779,762  1/1957  Robertson et al. ................. 549/285

Primary Examiner—Frederick E. Waddell
Attorney, Agent, or Firm—Hurt, Richardson, Garner, Todd & Cadenhead

[57] ABSTRACT

Substituted isocoumarins, their use in inhibiting serine proteases with trypsin-like, chymotrypsin-like and elastase-like specificity and their roles as anticoagulant agents, and anti-inflammatory agents.

9 Claims, No Drawings

ISOCOUMARINS WITH BASIC SUBSTITUENTS AS SERINE PROTEASES INHIBITORS, ANTICOAGULANTS AND ANTI-INFLAMMATORY AGENTS

STATEMENT OF GOVERNMENT INTEREST

This invention was made with government support under Contract No. HL 34035 awarded by the National Institutes of Health, National Heart, Lung and Blood Institute. The government has certain rights in the invention.

This application is a continuation-in-part of application Ser. No. 043,647, filed on Apr. 28, 1987, now issued as U.S. Pat. No. 4,845,242 on July 4, 1989.

BACKGROUND OF THE INVENTION

1. Field of the Invention

This invention relates to a novel class of heterocyclic compounds useful for selectively inhibiting trypsin-like enzymes, selectively inhibiting chymotrypsin-like enzymes, selectively inhibiting elastase or for generally inhibiting serine proteases of all classes. This invention also relates to a method of controlling blood coagulation, tumor invasiveness and treating inflammation in patients using the novel compounds of the present invention. We have found that substituted isocoumarins are potent inhibitors of blood coagulation enzymes, complement enzymes, tryptases, kallikreins, plasmin, chymases and elastase, therefore they are useful as anticoagulants, anti-inflammatory and anti-tumor agents.

2. Description of the Related Art

Serine proteases play critical roles in several physiological processes such as digestion, blood coagulation, complement activation, fibrinolysis, and reproduction. Serine proteases are not only a physiological necessity, but also a potential hazard if they are not controlled. Blood coagulation serine proteases are responsible for vascular clotting, cerebral infarction, and cornary infarction. Plasmin and plasminogen activator are involved in tumor invasiveness, tissue remodeling, and clot dissociation. Abnormal activation of complement enzymes may cause autoimmune hemolytic anemia, autoimmune thermocytopenia, leukopenia, glomerulonephritis, systemic lupus erythematosus, serum sickness and periateritis nodosa. Uncontrolled proteolysis by elastases may cause pancreatitis, emphysema, rheumatoid arthritis, bronchial inflammation and adult respiratory distress syndrome. Accordingly, specific and selective inhibitors of these proteases should be potent anticoagulants, anti-inflammatory agents and anti-tumor agents useful in the treatment of protease-related diseases (Powers and Harper, in Proteinase Inhibitors, Barrett and Salvesen, eds., Elsevier, 1986, pp 55-152, incorporated herein by reference). In vitro proteolysis by trypsin, chymotrypsin or the elastase family is a serious problem in the production, purification, isolation, transport or storage of peptides and proteins.

Anticoagulants and antithrombotic drugs are used in a variety of thrombotic disorders. The 1986 Physician's Desk Reference list three anticoagulant drugs (heparin, protamine sulfate and warfarin), one antiplatelet drus (aspirin) and several thrombolytic agents. Heparin and warfarin are commonly used clinically for prevention and treatment of venous thrombosis and pulmonary embolism. Heparin inhibits the blood coagulation activity by accelerating the binding of natural plasma protease inhibitor antithrombin III with coagulation factors, and warfarin acts as a vitamin K antagonist and inhibits the synthesis of coagulation factors. None of the anticoagulant drugs, antithrombotic drugs, fibrinolytic agents and antiplatelet drugs are highly effective in all clinical situations and many induce side reactions (Von Kaulla in Burger's Medicinal Chemistry, Part II, Wolff ed, 1979, pp 1081-1132, incorporated herein by reference). Coagulation disorders such as disseminated intravascular coagulation, bleeding complications of medical and surgical procedures and bleeding complications of systemic illness are still difficult to manage (Ingram, Brozovic and Slater in Bleeding Disorders, Blackwell Scientific Publications, 1982, pp 1-413). In the treatment of patients with coagulation problems, anticoagulant or antithrombotic agents of diverse mechanisms are urgently sought in order to provide better medical care.

Anti-inflammatory agents were used to treat elastases-associated inflammation including rheumatoid arthritis and emphysema. Although the naturally occurring protease inhibitor, $\alpha$1-protease inhibitor ($\alpha$1-PI) has been used to treat patients with emphysema, this inhibitor is not widely used clinically due to the high dosage needed for the treatment and difficulty of producing large quantities. Therefore small molecular weight elastase inhibitors are needed for therapy.

SUMMARY OF THE INVENTION

It is an object of this invention to find a novel group of specific inhibitors for trypsin, elastase, chymotrypsin and other serine proteases of similar substrate specificity and for serine proteases in general. Inhibitors are compounds that reduce or eliminate the catalytic activity of the enzyme. Trypsin and trypsin-like enzymes normally cleave peptide bonds in proteins and peptides where the amino acid residue on the carbonyl side of the split bond ($P_1$ residue) is Lys or Arg. Elastase and elastase-like enzymes, on the other hand, cleave peptide bonds where the $P_1$ amino acid is Ala, Val, Ser, Leu and other similar amino acids. Chymotrypsin and chymotrypsin-like enzymes hydrolyze peptide bonds where $P_1$ amino acid is Trp, Tyr, Phe, Met, Leu or other amino acid residues which contain aromatic or large alkyl side chains. All of the above enzymes have extensive secondary specificity and recognize amino acid residues removed from the $P_1$ residue.

It is an object of this invention to discover new protease inhibitors, especially blood coagulation enzyme inhibitors, which can act as anticoagulants in vitro and in vivo. Such inhibitors could be used in prevention of thrombosis during periods of stasis and/or endothelial damage in the segments of vasculature. They could also be used in an adjunct to fibrinolytic therapy to prevent acute coronaries or peripheral arteries reclosure. The inhibitors of this invention would be useful as the sole method of maintaining anticoagulation in extracorporeal blood circuits such as the kidney hemodialysis, and heart lung bypass. Such inhibitors could also be used as alternate anticoagulants when conventional anticoagulation with heparin or coumarin fail or is contraindicated. The inhibitors of this invention would also be useful in the therapy for disseminated intravascular coagulation syndromes (DIC). They could also be used in prophylaxis against thrombosis in high risk situation involving myocardium (e.g. unstable angina).

It is another object of this invention to discover new protease inhibitors, especially elastase inhibitors, complement enzyme inhibitors, tryptase inhibitors, chymase inhibitors and plasmin inhibitors. These inhibitors are useful for controlling tissue damage and various inflammatory conditions mediated by proteases particularly elastases. The inhibitors of this invention would be useful for treating diseases relates to complement proteases or plasmin; such as autoimmune diseases and tumor invasiveness. The inhibitors of this invention would also be useful for controlling hormone processing by serine proteases and for treating diseases related to tryptases and chymases such as inflammation and skin blistering.

It is a further object of this invention to find a novel group of specific inhibitors useful in vitro for inhibiting trypsin, elastase, chymotrypsin and other serine proteases of similar specificity and for inhibiting serine proteases in general. Such inhibitors could be used to identify new proteolytic enzymes encountered in research. They could also be used in research and industrially to prevent undesired proteolysis that occurs during the production, isolation, purification, transport and storage of valuable peptides and proteins. Such proteolysis often destroys or alters the activity and/or function of the peptides and proteins. Uses would include the addition of the inhibitors to antibodies, enzymes, plasma proteins, tissue extracts or other proteins and peptides which are widely sold for use in clinical analyses, biomedical research, and for many other reasons. For some uses a specific inhibitor would be desirable, while in other cases, an inhibitor with general specificity would be preferred.

DETAILED DESCRIPTION OF THE INVENTION

Substituted isocoumarins have been found to be excellent inhibitors of several serine proteases including bovine thrombin, bovine factor Xa, human factor Xa, human factor XIa, human factor XIIa, human factor VIIa, human plasma kallikrein, porcine pancreatic kallikrein, brovine trypsin, human plasma plasmin, human tissue plasminogen activator, sheep lung lymph tryptase, human lung tryptase, rat skin tryptase, human complement proteins $C1\bar{r}$, $C1\bar{s}$, D, B, C2, human leukocyte elastase, porcine pancreatic elastase, bovine chymotrypsin and human leukocyte cathepsin G, rat mast cell protease II, human skin chymase, human lung chymase, mouse cytotoxic T lymphocyte granzyme A, human cytotoxic T lymphocyte granzyme A and human Q31 cytotoxic T lymphocyte tryptase. These compounds inhibit the serine proteases by reaction with the active site serine to form an acyl enzyme, which in some cases may further react with another active site nucleophile to form an additional covalent bond. These structures may be used in vivo to treat diseases resulting from abnormal complement activation or uncontrolled blood coagulation or diseases caused by untrolled proteolysis by elastase, chymotrypsin, trypsin and related serine proteases. These inhibitors may be used in vitro to prevent proteolysis which occurs in the process of production, isolation, purification, storage or transport of peptides and proteins. The novel substituted isocoumarin and related heterocycic compounds have the following structural formula:

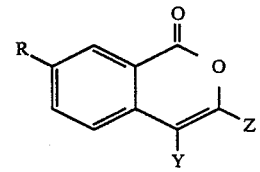

or a pharmaceutically acceptable salt thereof, wherein

R is selected from the group consisting of —NH—C(=NH)NH₂, —C(=NH)NH₂, amino-$C_{1-6}$ alkyl, and $C_{1-6}$ alkyl with an isotheiureido group of the formula —S—C(=NH)NH₂ attached to the alkyl group, Z is selected from the group consisting of H, halogen, $C_{1-6}$ alkyl, $C_{1-6}$ alkyl with a phenyl group attached to the alkyl group, $C_{1-6}$ fluorinated alkyl, $C_{1-6}$ alkyl with a hydroxyl group attached to the alkyl group, $C_{1-6}$ alkyl with a $C_{1-6}$ alkoxy attached to the alkyl group, $C_{1-6}$ alkoxy, $C_{1-6}$ fluorinated alkoxy, $C_{1-6}$ alkoxy with a phenyl group attached to the alkoxy group, benzyloxy group wherein the phenyl group is unsubstituted or substituted by one or two substituents selected from halogen, trifluoromethyl, NO₂, cyano, methyl, methoxy, acetyl, carboxyl, OH, and amino, and Y is selected from the group consisting of H, halogen, trifluoromethyl, methyl, OH, and methoxy.

Alternately the novel isocoumarin and related heterocyclic compounds are represented by structure (I) where, Z is selected from the group consisting of $C_{1-6}$ alkoxy with an amino group attached to the alkoxy group, $C_{1-6}$ alkoxy with an isothiureido group attached to the alkoxy group, $C_{1-6}$ alkoxy with a guanidino group attached to the alkoxy group, $C_{1-6}$ alkoxy with an amidino group attached to the alkoxy group, $C_{1-6}$ alkyl with an amino group attached to the alkyl group, $C_{1-6}$ alkyl with an isothiureido group attached to the alkyl group, $C_{1-6}$ alkyl with a guanidino group attached to the alkyl group, $C_{1-6}$ alkyl with an amidino group attached to the alkyl group, R is selected from the group consisting of H, OH, NH₂, NO₂, halogen, $C_{1-6}$ alkoxy, $C_{1-6}$ fluorinated alkoxy, $C_{1-6}$ alkyl, amino-$C_{1-6}$ alkyl, M—AA—NH—, M—AA—O—, wherein AA represents alanine, valine, leucine, isoleucine, proline, methionine, phenylalanine, tryptophan, glycine, serine, theonine, cysteine, tyrosine, asparagine, glutamine, aspartic acid, glutamic acid, lysine, arginine, histidine, beta-alanine, norleucine, norvaline, alpha-aminobutyric and epsilon-aminocaproic acid, citrulline, hydroxyproline, ornithine and sarcosine, wherein M represents H, lower alkanoyl having 1 to 6 carbons, carboxyalkanoyl, hydroxyalkanoyl, aminoalkanoyl, benzene sulfonyl, tosyl, benzoyl, and lower alkyl sulfonyl having 1 to 6 carbons, and Y is selected from the group consisting of H, halogen, trifluoromethyl, methyl, OH and methoxy.

Alternately the novel isocoumarin and related heterocyclic compounds are represented by structure (I) wherein, R is selected from the group consisting of —NH—C(=NH)NH₂, —(=NH)NH₂, amino-$C_{1-6}$ alkyl, isothiureido-$C_{1-6}$ alkyl, Z is selected from the group consisting of $C_{1-6}$ alkoxy with an amino group attached to the alkoxy group, $C_{1-6}$ alkoxy with an isothiureido group attached to the alkoxy group, $C_{1-6}$ alkoxy with a guanidino group attached to the alkoxy group, $C_{1-6}$ alkoxy with an amidino group attached to the alkoxy group, $C_{1-6}$ alkyl with an amino group attached to the alkyl group, $C_{1-6}$ alkyl with an isothiureido group attached to the alkyl group, $C_{1-6}$ alkyl with a guanidino group attached to the alkyl group, $C_{1-6}$ alkyl with an amidino group attached to the alkyl group, and Y is selected from the group consisting of H, halogen, trifluoromethyl, methyl, OH and methoxy.

Other substituted isocoumarins have been prepared earlier for other purposes (illustrative examples: Davies and Poole, J. Chem. Soc., pp 1616–1629 (1928); Milevskaya, Belinksaya, and Yagupol'skii, Zhur. Org. Khim. 9, pp 2145–2149 (1973); Tirodkar and Usgaonkar, Ind. J. Chem. 7, pp 1114–1116 (1969); Choksey and Usgaonkar, Ind. J. Chem. 14B, pp 596–598 (1976), the preceding articles are incorporated herein by reference).

A number of other substituted isocoumarins have been prepared recently for inhibition of serine proteases (Harper, Hemmi, and Powers, J. Am. Chem. Soc. 105, pp 6518–6520 (1983); Harper, Hemmi, and Powers, Biochemistry 24, pp 1831–1841 (1985); Harper and Powers, J. Am. Chem. Soc. 106, pp 7618–7619 (1984); Harper and Powers, Biochemistry 24, 7200–7213 (1983); Kam, Fujikawa and Powers, Biochemistry 27, pp 2547–2557 (1988); Powers, Kam, Narasimhan, Oleksyszyn, Hernandez and Ueda, J. Cell Biochem. 39, pp 33–46 (1989), the preceding articles are incorporated herein by reference; and Powers and Harper, U.S. Pat. No. 4,596,822, which is also incorporated by reference).

The following compounds are representative of the invention:

3-(3-aminopropoxy)isocoumarin
3-(3-aminopropoxy)-4-chloroisocoumarin
3-(2-isothiureidoethoxy)-4-chloroisocoumarin
3-(3-isothiureidopropoxy)-4-chloroisocoumarin
7-amino-3-(2-isothiureidoethoxy)-4-chloroisocoumarin
7-amino-3-(3-isothiureidopropoxy)-4-chloroisocoumarin
7-guanidino-3-methoxyisocoumarin
7-guanidino-3-methoxy-4-chloroisocoumarin
7-guanidino-3-ethoxyisocoumarin
7-guanidino-3-ethoxy-4-chloroisocoumarin
7-guanidino-3-(2-phenylethoxy)isocoumarin
7-guanidino-3-(2-phenylethoxy)-4-chloroisocoumarin
7-(alanylamino)-3-methoxy-4-chloroisocoumarin
7-(glycylamino)-3-methoxy-4-chloroisocoumarin It has been found that compounds of Formula (I) have anticoagulant activity as shown in Table I by effective inhibition of the proteolytic function of blood coagulation enzymes in Hepes buffer. Compounds of Formula (I) also have anticoagulent effect in vitro as shown in Table IX by prolongation of the prothrombin time (PT) and activated partial thromboplastin time (APTT) in human and rabbit plasma. It has also been found that compounds of Formula (I) have anticoagulant effect in vivo as shown in Table X and Table XI by prolongation the APTT with continuous infusion of 7-amino-3-(3-isothiureidopropoxy)-4-chloroisocoumarin into rabbits.

It has been found that compounds of Formula (I) are effective in the treatment of organ rejection and autoimmune diseases as shown in Table II by the effective inhibition of the proteolytic function of complement proteins. Compounds of Formula (I) are effective in the detection, prevention and inhibition of adult and infantile respiratory distress syndrome (a consequence of acute lung injuries) as shown in Table III by the effective inhibition of the proteolytic function of sheep lung lymph tryptase and human lung tryptase. Sheep lung lymph tryptase is utilized as a marker of lung capillary injury, and this is shown in the articles by Lesser et al., Am. Rev. Respir. Dis. 135, pp 643–650 (1987) and by Orlowski et al., Arch. Biochem. Biophys. 269, pp 125–136 (1989), which are incorporated herein by reference. Compounds of Formula (I) have anti-inflammatory activity and are effective in the prevention and inhibition of edema and granuloma tissue formation as shown in Table IV by the effective inhibition of the proteolytic function of human leukocyte elastase. Compounds of Formula (I) are effective in treating a variety of blistering diseases as shown in Table III and Table V by the effective inhibition of proteolytic function of rat skin tryptase and human skin chymase. It has been found that compounds of Formula (I) have anti-tumor activity as shown in Table VI by the effective inhibition of the proteolytic function of human plasma plasmin and human tissue plasminogen activator.

Inactivation rates of serine proteases by substituted isocoumarins were measured by the incubation method. An aliquot of inhibitor (25 or 50 µl) in Me$_2$SO was added to a buffered enzyme solution (0.01–2.3 µM) to initiate the inactivation. Aliquots (50 µl) were withdrawn at various intervals and the residual enzymatic activity was measured. Me$_2$SO concentration in the reaction mixture was 8–12% (v/v). 0.1 Hepes, 0.01M CaCl$_2$, pH 7.5 buffer was utilized for trypsin and coagulation enzymes. 0.1M Hepes, 0.5M NaCl, pH 7.5 was utilized for other serine proteases. The inhibitor concentrations are shown in the Tables I, II, III, IV, V, VI, and VII. Peptide thioesters or peptide nitroanilides with appropriate sequence were used as substrates for various serine proteases. All peptide thioester hydrolysis rates were measured with assay mixtures containing 4,4'-dithiodipyridine ($\epsilon_{324}=19800M^{-1}cm^{-1}$; Grasetti & Murray, Arch. Biochem. Biophys. 119, pp 41–49 (1967)). Peptide 4-nitroanilide hydrolysis was measured at 410 nm ($\epsilon_{410}=8800M^{-1}cm^{-1}$; Erlanger et al., Arch. Biochem. Biophys. 95, pp 281–278 (1961)). First order inactivation rate constant ($k_{obs}$) were obtained from plots of ln $v_t/v_o$ vs time, and the correlation coefficients were greater than 0.98.

Table I shows the inactivation rate constants for several trypsin-like serine proteases inhibited by substituted isocoumarins. When the isocoumarin structure contains basic functional groups such as guanidino as R, or amino-alkoxy, isothiureidoalkoxy as Z, and Cl as Y, the compound is generally a good inhibitor for trypsin and blood coagulation enzymes and tryptases. The inactivation of the enzyme is time dependent, and the $k_{obs}/[I]$ values are second order rate constants. In most cases, inactivation of the enzyme occurs at the inhibitor concentration of 5–400 times the enzyme concentration and the first order rate constant $k_{obs}$ is obtained. However, in some cases, the inactivation was too fast to be measured under first order rate condition ([I]>[E]), the inactivation rate was measured either in the presence of substrate using the progress curve method as described by Tian and Tsou, Biochemistry 21, pp 1028–1032 (1982) or using the same concentration of enzyme and inhibitor. 7-guanidino-4-chloro-3-alkoxyisocoumarins are essentially stoichiometric inactivators of trypsin, thrombin and kallikrein. The inactivation rate of the enzyme depends on the substituents R, Z and Y. The structures with R groups of guanidino, and Y groups of Cl are the best inhibitors for trypsin and all the coagulation enzymes tested. The isocoumarins with Y groups of Cl and Z groups of isothiureidoalkoxy are potent inhibitors toward trypsin-like enzymes.

Table II shows the inactivation of complement proteins D, B, C2, C1r̄, C1s̄, and their active fragments C2a, Bb by substituted isocoumarins. The isocoumarin with R groups of amino or hydrogen, Z groups of isothiureidopropoxy, and Y groups of chloro inhibit C1r̄ and C1s̄ quite potently. 7-Guanidino-3-alkoxy-4-chloroisocoumarin inhibit C1r̄, C1s̄, B and Bb moderately. Although 3-isothiureidoalkoxy-4-chloroisocoumarins inhibit protein B and C2 poorly, while other serine protease inhibitors such as 4-amidinophenylmethane sulfonyl fluoride (APMSF) and 3,4-dichloroisocoumarin do not show any inhibition toward these two enzymes. Table III shows the inactivation of sheep lung lymph tryptase, human lung tryptase and rat skin tryptase by substituted isocoumarins. The structure with R group of guanidino, Z group of alkoxy, and Y group of chloro are good inhibitors for sheep lung lymph tryptase. The isocoumarins with R groups of guanidino or amino, Z groups of alkoxy or isothiureidopropoxy, and Y groups of chloro are potent inhibitors for human lung tryptase and rat skin tryptase. Table IV shows the inactivation rate constants for porcine pancreatic elastase (PPE), human leukocyte elastase (HLE), chymotrypsin and cathepsin G inhibited by substituted isocoumarins. Although the inactivation by the inhibitors was less efficient toward these four enzymes than trypsin-like enzymes, the isocoumarin with R group of guanidino, Y group of Cl, and Z-group of ethoxy is a good inhibitor for PPE, HLE and cathepsin G. The structure with Z-group of 2-phenylethoxy is best at inhibiting chymotrypsin.

Table V shows the inactivation of rat mast cell protease II, human skin chymase and human lung chymase by substituted isocoumains. The structure with R group of guanidino, Z group of alkoxy, and Y group of chloro werre potent inhibitors for rat mast cell protease II and were moderate inhibitors for human skin chymase and human lung chymase. Table VI shows the inactivation rate constants for human plasmin and human tissue plasminogen activator by substituted isocoumarins. The structure with R groups of amino, hydrogen or guanidino, Z groups of isothiureidoalkoxy or alkoxy, and Y groups of chloro inhibited both enzymes potently. Table VII shows the inactivation of mouse granzyme A, human granzyme A and human Q31 tryptase by substituted isocoumarins. The isocoumarins with R groups of hydrogen, amino or guanidino, Z groups of isothiureidoalkoxy or alkoxy, and Y groups of chloro were potent inhibitors for all three tryptases.

The spontaneous hydrolysis rates of these substituted isocoumarins in Hepes buffer, human and rabbit plasma have been measured and summarized in Table VIII. The isocoumarins with hydrogen at position 4 are 3-6 times more stable than the compounds with Cl at the same position. 7-Amino-4-chloro-3-(3-isothiureidopropoxy)isocoumarin is fairly stable in both human and rabbit plasma. 7-Guanidino-4-chloro-3-alkoxyisocoumarins are hydrolyzed in human and rabbit plasma with half-lives of 5-8 min.

Table IX shows the anticoagulant effect of substituted isocoumarins in human and rabbit plasma. The prothrombin time (PT) and activated partial thromboplastin time (APTT) were measured in the presence of various inhibitors. 7-Guanidino-3-ethoxy-4-chloroisocoumarin and 7-amino-3-(3-isothiureidopropoxy)-4-chloroisocoumarin show more effect on APTT than PT. With normal citrated human plasma, 7-guanidino-3-ethoxy-4-chloroisocoumarin prolong PT 1.8 fold and prolong APTT more than 4.5 fold at 21 μM, and 7-amino-3-(3-isothiureidopropoxy)-4-chloroisocoumarin prolong APTT more than 4.5 fold and increase PT 1.5 fold at 29 μM. Both compounds have smaller effect in rabbit plasma.

Table X shows the dose-response data of 7-amino-3-(3-isothiureidopropoxy)-4-chloroisocoumarin on APTT when this compound was administered into rabbits with continuous infusion. 7-Amino-3-(3-isothiureidopropoxy)-4-chloroisocoumarin prolonged the APTT two fold over control values at lowest dose of 0.4 mg/ml, whereas at the highest dose of 1.2 mg/ml the APTT is prolonged 3 to 4 times control. Table XI shows the APTT and activated clotting time (ACT) of 7-amino-3-(3-isothiureidopropoxy)-4-chloroisocoumarin with a continuous infusion of 0.8 mg/ml to rabbits for 17 min. At 16 min during the infusion, this compound prolongs APTT 2.3 fold and prolongs ACT 1.4 fold.

Anticoagulants can prolong the clotting time of human plasma and play important roles in the treatment of blood coagulation related diseases such as vascular clotting, cerebral infarction and cornary infarction (Williams et al., Hemotalogy, 3rd ed. McGraw Hill, 1983 and Ingram et al., Bleeding Disorders, 2nd ed. Blackwell Scientific Publications, 1985. These two books are incorporated herein by reference). The prescence of certain inhibitors of this invention in the human and rabbit plasma prolong the prothrombin time and activated partial thromboplastin time quite effectively, therefore these compounds act as anticoagulants in vitro. One of these isocoumarins, 7-amino-3-(3-isothiureidopropoxy)-4-chloroisocoumarin also showed prolongation on APTT when it was administered into rabbits with continuous infusion. Thus these inhibitors would act as anticoagulants in vivo. Currently, there are a few anticoagulant and antithrombotic drugs in use clinically, and the inhibitors described in this invention can be used as anticoagulants or antithrombotics in the treatment of mammals (including man).

It is known that in vitro activity of elastase inhibitors correlates with in vivo activity in animal models of emphysema and inflammation (Otterness et al., editor, Advances in Inflammation Research, Vol. 11, Raven Press 1986, and this article is incorporated herein by reference). Thus the novel inhibitors described here should be useful for the treatment of emphysema and inflammation. Elastase inhibitors have been used orally, by injection or by instillation in the lungs in animal studies (Powers, Am. Rev. Respir. Dis., 127, s54-s58 (1983); Powers and Bengali, Am. Rev. Respir. Dis. 134, pp 1097-1100 (1986) and these two articles are incorporated herein by reference). The inhibitors described above can be used by any of these routes.

For treatment of blood coagulation-related diseases, tumor invasiveness or inflammation, the compounds of Formula (I) or pharmaceutically acceptable salts may be administered orally, topically or parenterally. The term parenteral as used includes subcutaneous injection, intravenous, intramuscular, intrasternal injection or infusion techniques. The dosage depends primarily on the specific formulation and on the object of the therapy or prophylaxis. The amount of the individual doses as well as the administration is best determined by individually assessing the particular case.

The pharmaceutical compositions containing the active ingredient may be in a form suitable for oral use, for example as tablets, troches, lozenges, aqueous or oily suspensions, dispersible powders or grannules, emulsions, hard or soft capsules or syrups or elixirs. Dosage levels of the order to 0.2 mg to 140 mg per kilogram of body weight per day are useful in the treatment of above-indicated conditions (10 mg to 7 gms per patient per day). The amount of active ingredient that may be combined with carrier materials to produce a single dosage form will vary depending upon the host treated and the particular mode of administration.

For injection, the therapeutic amount of the compounds of Formula (I) or their pharmaceutically acceptable salts will normally be in the dosage range from 0.2 to 140 mg/kg of body weight. Administration is made by intravenous, intramuscular or subscutaneous injection. Accordingly, pharmaceutical compositions for parenteral administration will contain in a single dosage form about 10 mg to 7 gms of compounds of Formula (I) per dose. In addition to the active ingredient, these pharmaceutical compositions will usually contain a buffer, e.g. a phosphate buffer which keeps the pH in the range from 3.5 to 7 and also sodium chloride, mannitol or sorbitol for adjusting the isotonic pressure.

A composition for topical application can be formulated as an aqueous solution, lotion, jelly or an oily solution or suspention. A composition in the form of an aqueous solution is obtained by dissolving the compounds of Formula (I) or their pharmaceutically acceptable salts in aqueous buffer solution of pH 4 to 6.5 and if desired, adding a polymeric binder. An oily formulation for topical application is obtained by suspending the compounds of Formula (I) or their pharmaceutically acceptable salts in an oil, optionally with the addition of a swelling agent such as aluminium stearate and/or a surfactant.

In addition to the compounds of Formula (I) or their pharmaceutically acceptable salts which are intended for medicinal use on the human or animal body, the present invention also relates to the compounds of Formula (I) or their pharmaceutically acceptable salts for the medicinal use outside the living body of humans or animals. Such compounds are used as anticoagulants for blood which is subjected to extracorporeal circulation or treatment such as kidney hemodialysis, heat lung bypass, or ultrafiltration. Such preparation are similar in composition and are similar to the above described injection preparations. However, the amount of active ingredient is conveniently based on the volume of the blood to be treated. In such treatment, the compound of Formula (I) or their pharmaceutically acceptable salts must be eilminated from the blood rapidly even in large concentration so that there is no danger of overdosage. Depending on the specific purpose, the suitable dose is from 2 mg to 1.4 gms of the active ingredient per liter of blood.

To use the above inhibitors in vitro, they are dissolved in an organic solvent such as dimethylsulfoxide or ethanol, and are added to an aqueous solution containing serine proteases. The final concentration of the organic solvent should be less than 25%. The inhibitors may also be added as solids or in suspension. The serine protease inhibitors of this invention would be useful in a variety of experimental procedures where proteolysis is a significant problem. Inclusion of these inhibitors in a radioimmunoassay experiments would result in higher sensitivity. The use of these inhibitors in plasma frac- tionation procedures would result in higher yields of valuable plasma proteins and would make purification of the proteins easier. The inhibitors disclosed here could be used in cloning experiments utilizing bacterial cultures, yeast and purified cloned product in higher yield.

The following examples are given to illustrate the invention and are not intended to limit it in any manner.

EXAMPLE 1

Preparation of 3-(2-Isothiureidoethoxy)-4-Chloroisocoumarin

2-Bromoethyl 2-carboxyphenylacetate was prepared from heating 10 g of homophthalic acid (56 mmole) and 21 g of 2-bromoethanol (167 mmole) in 175 ml of benzene with a few drops of conc. sulfuric acid at 90°-110° C. for two hours, yield 64%. TLC shows that it is a pure compound. The cyclization of 2-bromoethyl 2-carboxyphenylacetate with $PCl_5$ was performed by a previous method with modification (Tirodkar, and Usgaonkar, Indian. J. Chem. 7, pp 114–1116 (1969)). 1.15 g of 2-bromoethyl 2-carboxyphenylacetate was heated with 2.1 g of $PCl_5$ in 90 ml of benzene at 70° C. for 2 hrs. The benzene was removed and the residue triturated with petroleum ether. The crude product was purified by silica gel column chromatography with methylene chloride as an eluent to give 560 mg of 3-(bromoethyl)-4-chloroisocoumarin (yield, 46%). IR and NMR spectra show it was the desired product. 100 mg of 3-bromoethyl-4-chloroisocoumarin (0.3 mmole) was heated with 60 mg of thiourea (0.8 mmole) in 5 ml of THF at 70° C. for 2 days to give a yellow solid, 50 mg (yield, 40%), m.p. 167°–169° C. (dec); one spot on TLC, $RF=0.7$ (Butanol:acetic acid:water=6:1:5); NMR spectrum ($d_6$-DMSO), δ9.1 (2b, 4H), 7.5–8.1 (m, 4H), 4.6 (t, 2H), 3.6 (t, 2H); mass spectrum (FAB+), m/e=299 (M+-Br). Anal. Calc. for $C_{12}H_{12}N_2O_3Br_1Cl_1S_2$: C, 37.96; H, 3.19; N, 7.38. Found: C, 37.81; H, 3.28; N, 7.71.

EXAMPLE 2

Preparation of 7-Guanidino-3-Methoxyisocoumarin

Methyl 2-carboxy-4-nitrophenyl acetate was prepared from 2-carboxy-4-nitrophenylacetate and methanol by the procedure described above. Hydrogenation of this nitro compound gives methyl 4-amino-2-carboxy-phenylacetate (yield 90%). The guanidination of the amino compound with 3,5-dimethylpyrazole-1-carboxamidine nitrate (ADMP) was preformed by a standard method described previously (Tsunematsu & Makismi, J. Biochem. 88, pp 1773–1783, (1980)). 2.2 g of amino compound (10 mmole), 1.9 g of triethylamine (19 mmole) and 3.0 g of ADMP (15 mmole) was heated in 20 ml of THF and refluxed for 18 hrs. The white precipitate was filtered and washed with cold methanol to give 1.5 g of methyl 2-carboxy-4-guanidinophenylacetate, (yield 46%). One spot on TLC, $Rf=0.6$ (Butanol:acetic acid:pyridine:water=4:1:1:2), it shows an orange color when sprayed with Sakaguchi reagent. NMR spectrum ($CF_3COOH$), δ8.4, 7.7 (b, 4H), 6.6 (b, 4H) 4.4 (s, 2H), 4.1 (s, 3H). Anal. Calc. for $C_{11}H_{13}N_3O_4 \cdot \frac{1}{2}H_2O$: C, 50.77; H, 5.42; N, 16.15. Found: C, 51.03; H, 5.38; N, 16.19. 0.9 g of methyl 2-carboxy-4-guanidinophenylacetate (3 mmole) was heated with 1.5 g of $PCl_5$ (7.2 mmole) at 70°–80° C. for 2 hrs, white solid precipitated out during the heating. The solid was filtered off and purified by silica gel column chromatography with methylene chloride and methanol (5:1) as an eluent to give 0.5 g of 7-guanidino-3-methoxyisocoumarin (yield 59%). One spot on TLC, Rf=0.7 (Butanol:acetic acid:-pyridine:water=4:1:1:2); m.p. 185°–186° C. (dec);, NMR spectrum (d$_6$-DMOS): δ7.9, 7.6 (b, 3H), 7.7 (b, 4H), 6.1 (s, 1H), 3.9 (s, 3H); mass spectrum (FAB+), m/e=234 (M+-Cl). Anal. Calc. for C$_{11}$H$_{12}$N$_3$O$_3$Cl$_1$.½H$_2$O: C, 47.40; H, 4.67; N, 15.08; Cl, 12.75. Found: C, 47.42; H, 4.74; N, 15.05; Cl, 12.68.

EXAMPLE 3

Preparation of
7-Guanidino-3-Methoxy-4-Chloroisocoumarin 0.27 g of 7-guanidino-3-methoxyisocoumarin (1 mmole) was chlorinated with 0.15 g of N-chlorosuccinimide (1.1 mmole) in 5 ml DMF at r.t. overnight. The reaction mixture was evaporated to dryness, and purified by silica gel column chromatography which is eluted with methylene chloride and methanol (5:1) to give 0.1 g of 7-guanidino-3-methoxy-4-chloroisocoumarin (yield 34%). One spot on TLC, Rf=0.75 (Butanol:acetic acid:pyridine:water=4:1:1:2); NMR spectrum is similar to 7-guanidino-3-methoxyisocoumarin except no peak at 6.1 ppm; mass spectrum (FAB+), m/e=268 (M+-Cl). Anal. Calc. for C$_{11}$H$_{11}$N$_3$O$_3$Cl$_2$.½H$_2$O: C, 42.17; H, 3.83; N, 13.41; Cl, 22.68. Found: C, 42.65; H, 3.72; N, 13,28; Cl, 22.32.

EXAMPLE 4

Preparation of 3-(3-Aminopropoxy)isocoumarin Hydrochloride

Homophthalic acid (18 g, 0.1 mole) and 3-(benzyloxycarbonylamino)-1-propanol (41 g, 0.2 mole) were heated in 150 ml of benzene at 120°–130° C. for 2 hrs in the presence of a few drops of conc. H$_2$SO$_4$. Benzene was evaporated, and 200 ml of ethylacetate was added. The organic solution was washed with 4% NaHCO$_3$ twice (150 ml×2). The aqueous layer which contained the monoester salt was acidified with 5N HCl and extracted with ethylacetate. 33 g of 3-(benzyloxycarbonylamino)propyl 2-carboxyphenylacetate (yield, 89%) was obtained after the solvent was evaporated. Hydrogenation of this monoester (1.86 g, 5 mmole) was performed in methanol containing 0.3 ml of acetic acid and 10% palladium on carbon to give 1 g of 3-aminopropyl 2-carboxphenylacetate.HAc (yield, 67%). This compound was identified by its NMR spectrum and TLC (Butanol:acetic acid:pyridine:water=4:1:1:2). 1 g of 3-aminopropyl 2-carboxyphenylacetate.HAc (3 mmole) was heated with 1.6 g of PCl$_5$ (7.5 mmole) in 50 ml of anhydrous THF at 70°–80° C. for 2 hrs, a white precipitate formed. This white solid was purified by column chromatography (methylene chloride:methanol=5:1) and crystallized from MeOH-ether to give 0.2 g of 3-(3-aminopropoxy)isocoumarin.HCl (yield, 26%), m.p. 173°–174° C.; mass spectrum, m/e=220 (M+-Cl). Anal. Calc. for C$_{12}$H$_{14}$N$_1$O$_3$Cl$_1$: C, 56.37; H, 5.52; N, 5.48; Cl, 13.87. Found: C, 56.15; H, 5.49; N, 5.44; Cl 13.95.

EXAMPLE 5

Preparation of
3-(3-Aminopropoxy)-4-Chloroisocoumarin Hydrochloride 0.13 g of 3-(3-aminopropoxy)isocoumarin hydrochloride (0.5 mmole) was chlorinated with 0.007 g of N-chlorosuccinimide (0.5 mmole) in 5 ml of DMF at r.t. overnight. The reaction mixture was purified by silica gel column chromatography (methylene chloride:methanol=5:1) and crystallized from MeOH-ether to give 0.009 g of 3-(3-aminopropoxy)-4-chloro-isocoumarin hydrochloride (yield, 60%). The NMR spectrum of this compound is similar to 3-(3-aminopropoxy)isocoumarin without the peak at δ6.2 ppm; m.p. 160°–163° C.; mass spectrum, m/e=254 (M+-Cl). Anal. Calc. for C$_{12}$H$_{13}$N$_1$O$_3$Cl$_2$.¼H$_2$O: C, 48.88; H, 4.61; N, 4.75; Cl, 24.06. Found: C, 48.85; H, 4.54; N, 4.74; Cl, 24.02.

EXAMPLE 6

Preparation of
7-Amino-4-Chloro-3-(3-Isothiureidopropoxy)isocoumarin

This compound was synthesized by the same procedure as 3-(3-isothiureidopropoxy)-4-chloroisocoumarin. 3-Bromopropyl 2-carboxy-4-nitrophenylacetate was prepared from 2-carboxy-4-nitrophenylacetate and 3-bromopropanol, yield 60%. Cyclization of the monoester with PCl$_5$ gives 3-bromopropoxy-4-chloro-7-nitroisocoumarin (yield, 60%). Hydrogenation of the nitro compound (0.36 g) in methanol gives 0.12 g of 7-amino-3-bromopropoxy-4-chloroisocoumarin, which is purified by silica gel column chromatography with methylene chloride as an eluent (yield, 36%). This aminoisocoumarin reacts with thiourea in THF to give the final product, which can be crystallized from MeOH-ether (yield, 40%), mp 160°–162° C. (dec); one spot on TLC, Rf=0.6 (Butanol:acetic acid:pyridine water=4:1:1:2); mass spectrum (FAB+), m/e=328 (M+-Br). Anal. Calc. for C$_{13}$H$_{15}$N$_3$O$_3$Cl$_1$Br$_1$S$_1$: C, 38.20; H, 3.70; N, 10.28; Cl, 8.67. Found: C, 38.15; H, 3.73; N, 10.25; Cl, 8.63.

EXAMPLE 7

Preparation of
7-(Alanylamino)-3-Methoxy-4-Chloroisocoumarin Hydrochloride 7-(N-α-Boc-alanylamino)-3-methoxy-4-chloroisocoumarin was synthesized by reaction of Boc-Ala (1 g, 5.5 mmole) with 1,3-dicyclohexylcarbodiimide (0.57 g, 2.8 mmole) at 0° C. in THF for a few hours (DC Urea was precipitated out), followed by the addition of 7-amino-3-methoxy-4-chloroisocoumarin (0.5 g, 2.2 mmole). The reaction mixture was stirred at r.t. overnight, and DC Urea was then filtered. The reaction mixture was evaporated to dryness, redissolved in CH$_2$Cl$_2$ and washed with 4% NaHCO$_3$. After evaporating the sovent, the residue was crystallized in THF-Pet Ether to give 0.2 g of Boc-alanylisocoumarin compound, which was identified by NMR spectrum and was shown one spot on TLC. Boc-alanylisocoumarin (0.2 g) was stirred with 25 eq of TFA (1.4 g) in CH$_2$Cl$_2$ at r.t. for half hour and 1 eq of 3.8N HCl/dioxane was then added. The product was precipitated out when anhydrous ether was added, and was purified by column chromatography (CH$_2$Cl$_2$:MeOH=7:1), yield 0.1 g, one spot on TLC (CH$_2$Cl$_2$:MeOH=7:1), NMR (d$_6$-DMSO): δ7.4–8.4 (m, 3H), 4.0 (s, 3H), 3.1–3.6 (m, 1H), 1.5 (d, 3H).

EXAMPLE 8

In vivo Test of 7-Amino-3-(3-Isothiureidopropoxy)-4-Chloroisocoumarin

This compound was dissolved in dimethyl sulfoxide (Me$_2$SO) and diluted to a final concentration of 2% Me$_2$SO in normal saline. The inhibitor concentrations tested were from 0.4 mg/ml to 1.2 mg/ml. Fourteen New Zealand White rabbits weighing 2.5–3.5 kg were anesthetized with intramuscular injection of ketamine and xylazine. Via cutdown, the external jugular vein was cannulated for the infusions and the carotid artery was cannulated for blood draws. The animals were allowed to breathe spontaneously. The infusions of the inhibitor were given over a period of 13 to 15 minutes at a rate of 1 ml/min after a control APTT was drawn. 2 ml of blood was drawn at various time for the determination of APTT. The blood was placed in citrated tubes and centrifuged at 12,000 g for 4 minutes at room temperature. The platelet poor plasma thus obtained was placed on ice and APTT was determined in standard fashion and the data was shown in Table X. In another rabbit, the inhibitor was given at a concentration of 0.8 mg/ml over a 17 minute continuous infusion, and APTT and ACT were determined simultaneously at various time (data in Table XI).

TABLE I
Inactivation Rates for Inhibition of Trypsin-Like Serine Proteases by Substituted Isocoumarins[a]

$k_{obs}/[I]\ (M^{-1} s^{-1})$

| Inhibitors | bovine thrombin[b] | bovine factor X[c] | human factor Xa[d] | porcine pancreatic kallikrein[e] | human plasma kallikrein[f] | human factor XIa[g] | human factor XIIa[h] | bovine trypsin[i] | human factor VIIa[j] |
|---|---|---|---|---|---|---|---|---|---|
| 3-(3-aminopropoxy)-isocoumarin | 3.0 | NI[k] | | 5.0 | 30 | 30 | 3.0 | 1,200 | |
| 3-(3-aminopropoxy)-4-chloroisocoumarin | 350 | 160 | | 860 | 1,400 | 380 | 190 | 7,600 | |
| 3-(2-isothiureidoethoxy)-4-chloroisocoumarin | 4,700 | 5,600 | | 12,000 | 280,000[l] | 44,000 | 39,000 | 32,000 | |
| 3-(3-isothiureidopropoxy)-4-chloroisocoumarin | 1,430 | 220 | | 19,000 | >110,000[l] | 47,000 | 27,000 | 46,000 | 450 |
| 7-amino-3-(3-isothiureidopropoxy)-4-chloroisocoumarin | 630 | 1,640 | 60 | >110,000[m] | 1,100 | 22,000 | 6,200 | 410,000[n] | 430 |
| 7-guanidino-3-methoxy-isocoumarin | 4,900 | 460 | | 1,900 | 13,000 | 1,400 | 520 | 3,300 | |
| 7-guanidino-3-methoxy-4-chloroisocoumarin | 290,000[n] | 3,100 | 11,000 | 45,000[n] | 240,000[n] | 36,200 | 20,000 | 310,000[n] | |
| 7-guanidino-3-ethoxy-isocoumarin | 3,700 | 2,700 | | 16,000 | 44,000 | 3,100 | 1,300 | 20,000 | |
| 7-guanidino-3-ethoxy-4-chloroisocoumarin | >55,000[m] | 26,700 | 11,000 | >200,000[m] | >500,000[l] | 60,000 | 22,000 | >110,000[m] | 2,200 |
| 7-guanidino-3-(2-phenylethoxy)isocoumarin | 5,700 | 11,000 | | 16,000 | 62,000 | 1,200 | 690 | 45,000 | |
| 7-guanidino-3-(2-phenylethoxy)-4-chloroisocoumarin | >30,000[m] | 96,000 | 11,000 | 200,000[m] | >270,000[l] | 20,000 | 26,000 | 110,000[m] | |
| 7-(glycylamino)-3-methoxy-4-chloroisocoumarin | 51.5 | NI | | | | | | 32,100 | |
| 7-(alanylamino)-3-methoxy-4-chloroisocoumarin | NI | NI | | | | | | 470 | |

[a] Conditions were as 0.1 M Hepes, 0.01 CaCl$_2$, pH 7.5 and 8-12% Me$_2$SO and 25° C. Rate constants were measured by incubation method unless otherwise noted. An aliquot of inhibitor was added to an enzyme solution and aliquots removed with time and assayed for remaining enzymatic activity. First-order rate constants, $k_{obs}$ were obtained from the plots of ln $(v_t/v_o)$ versus time.
[b] Inhibitor concentrations were from 0.3 to 400 μM.
[c] Inhibitor concentrations were from 0.4 to 310 μM.
[d] Inhibitor concentrations were from 5 to 105 μM.
[e] Inhibitor concentrations were from 0.4 to 300 μM.
[f] Inhibitor concentrations were from 0.3 to 300 μM.
[g] Inhibitor concentrations were from 3 to 330 μM.
[h] Inhibitor concentrations were from 3 to 330 μM.
[i] Inhibitor concentrations were from 1 to 12 μM.
[j] Inhibitor concentrations were from 5 to 44 μM.
[k] No inhibition.
[l] Inactivation was extremely rapid, and the $k_{obs}/[I]$ values were based on the residual enzymatic activity at 0.2 min.
[m] Second-order rate constant was obtained from same concentration of enzyme and inhibitor.
[n] Inactivation rate constants were obtained by progress curve method described by Tian and Tsou, Biochemistry 21, 1028–1032 (1982).

TABLE II

Inactivation Rates of Inhibition of Complement Proteins by Substituted Isocoumarins and APMSF[a].

| Inhibitors | $k_{obs}/[I]$ (M$^{-1}$s$^{-1}$) | | | | | | |
|---|---|---|---|---|---|---|---|
| | D[b] | C2[c] | C2a[c] | B[c] | Bb[d] | C1s[-e] | C1r[-f] |
| APMSF | 110 | NI[g] | NI | NI | NI | | |
| 3,4-dichloroisocoumarin | 192 | NI | NI | NI | NI | 170 | 42 |
| 3-ethoxy-4-chloro-isocoumarin | 0.25 | NI | NI | NI | NI | | |
| 7-amino-3-methoxy-4-chloroisocoumarin | 1.3 | NI | NI | NI | NI | | |
| 3-(2-isothiureidoethoxy)-4-chloroisocoumarin | 61 | 1.5 | 1.4 | 13 | 15 | | |
| 3-(3-isothiureidopropoxy)-4-chloroisocoumarin | 145 | 0.5 | 0.8 | 0.4 | 0.8 | 130,000 | 6,610 |
| 7-amino-3-(3-isothiureido-propoxy)-4-chloro-isocoumarin | 55 | NI | | | NI | 23,000 | 1,320 |
| 7-guanidino-3-methoxy-4-chloroisocoumarin | 252 | NI | | 285 | 74 | 660 | 75 |
| 7-guanidino-3-ethoxy-4-chloroisocoumarin | 193 | NI | | 167 | 95 | 690 | 239 |
| 7-guanidino-3-(2-phenyl-ethoxy)-4-chloro-isocoumarin | 92 | NI | | | 58 | 90 | 342 |

[a]Conditions were 0.1 M Hepes, 0.5 M NaCl, pH 7.5, 8-10% Me$_2$SO and 25° C. Inactivation rates were measured by incubation method. Enzyme concentrations were as follows: protein D, 1-9 μM; C2, 0.7-1 μM; B, 1,8 μM; Bb 0.3-0.8 μM; C1s$^-$, 0.07 μM; C1r$^-$, 0.51 μM.
[b]Inhibitor concentrations were from 0.05 mM to 1.29 mM.
[c]Inhibitor concentrations were from 0.19 mM to 1.25 mM.
[d]Inhibitor concentrations were from 0.05 mM to 1.25 mM.
[e]Inhibitor concentrations were from 0.8 μM to 44 μM.
[f]Inhibitor concentrations were from 4.6 μM to 470 μM.
[g]No inhibition.

TABLE III

The Inactivation Rates of Sheep Lung Lymph Tryptase[a], Human Lung Tryptase[a] and Rat Skin Tryptase[b] by Substituted Isocoumarins.

| Inhibitors | $k_{obs}/[I]$ (M$^{-1}$s$^{-1}$) | | |
|---|---|---|---|
| | S. L. Tryptase[c] | H. L. Tryptase[d] | R. S. Tryptase[e] |
| 3,4-dichloroisocoumarin | 39 | 185 | 610 |
| 3-(3-aminopropoxy)isocoumarin | 8.1 | | |
| 3-(3-aminopropoxy)-4-chloroisocoumarin | 18 | 2,000 | 8,370 |
| 3-(2-isothiureidoethoxy)-4-chloro-isocoumarin | 290 | | |
| 3-(3-isothiureidopropoxy)-4-chloro-isocoumarin | 230 | 64,000 | 53,000 |
| 7-amino-3-(3-isothiureidopropoxy)-4-chloroisocoumarin | 710 | 28,000 | 63,000 |
| 7-guanidino-3-methoxyisocoumarin | 53 | | |
| 7-guanidino-3-methoxy-4-chloroisocoumarin | 620 | 20,000 | 52,000 |
| 7-guanidino-3-ethoxyisocoumarin | 150 | | |
| 7-guanidino-3-ethoxy-4-chloroisocoumarin | 2,200 | 61,000 | 82,000 |
| 7-guanidino-3-(2-phenylethoxy)isocoumarin | 150 | | |
| 7-guanidino-3-(2-phenylethoxy)-4-chloro-isocoumarin | 3,900 | 56,000 | 86,000 |
| APMSF[f] | 230 | | |

[a]Inactivation rates were measured at 0.1 M Hepes, 0.5 M NaCl, pH 7.5 buffer, 8% Me$_2$SO and 25° C.
[b]Inactivation rates were measured at 25 mM phosphate, 0.5 M NaCl, 1 mM EDTA, pH 7.5 buffer, 9% Me$_2$SO and 25° C.
[c]Inhibitor concentrations were from 10 μM to 460 μM.
[d]Inhibitor concentrations were from 0.4 μM to 40 μM.
[e]Inhibitor concentrations were from 0.4 μM to 50 μM.
[f]The inhibition rate was measured at 0.1 M Hepes, 0.5 M NaCl, pH 7.0, 25° C.

TABLE IV

Inactivation Rates for Inhibition of Serine Proteases by Substituted Isocoumarins[a]

| Inhibitors | $k_{obs}/[I]$ (M$^{-1}$s$^{-1}$) | | | |
|---|---|---|---|---|
| | PPE[b] | HLE[c] | Chymotrypsin[d] | Cathepsin G[e] |
| 3-(3-aminopropoxy)isocoumarin | 2.3 | 47 | 38 | 2.8 |
| 3-(3-aminopropoxy)-4-chloro-isocoumarin | 70 | 860 | 580 | 260 |
| 3-(2-isothiureidoethoxy)-4-chloro-isocoumarin | 270 | 220 | 1,300 | 110 |
| 3-(3-isothiureidopropoxy)-4-chloro-isocoumarin | 70 | 2,000 | 1,700 | 83 |
| 7-amino-3-(3-isothiureidopropoxy)-4-chloroisocoumarin | 1.0 | 630 | 4,400 | 36 |
| 7-guanidino-3-methoxyisocoumarin | 55 | 320 | 270 | —[f] |

TABLE IV-continued

Inactivation Rates for Inhibition of Serine Proteases by Substituted Isocoumarins[a]

| Inhibitors | $k_{obs}/[I]$ (M$^{-1}$s$^{-1}$) | | | |
|---|---|---|---|---|
| | PPE[b] | HLE[c] | Chymotrypsin[d] | Cathepsin G[e] |
| 7-guanidino-3-methoxy-4-chloro-isocoumarin | 860 | 6,400 | 7,200 | 11,000 |
| 7-guanidino-3-ethoxyisocoumarin | 86 | 1,900 | 990 | —[g] |
| 7-guanidino-3-ethoxy-4-chloro isocoumarin | 2,300 | 81,000 | 37,000 | 84,000 |
| 7-guanidino-3-(2-phenylethoxy)-isocoumarin | NI[h] | 0.89 | 2,600 | —[i] |
| 7-guanidino-3-(2-phenylethoxy)-4-chlorioscoumarin | 5.7 | 73 | 38,000 | 66,000 |
| 7-(glycylamino)-3-methoxy-4-chloroisocoumarin | 1,960 | 7,710 | | 4.9 |
| 7-(alanylamino)-3-methoxy-4-chloroisocoumarin | 1,610 | 13,500 | | 20 |

[a]Inactivation rates were measured at 0.1 M Hepes, 0.5 NaCl, pH 7.5, 8–12% Me$_2$SO and 25° C. by incubation method.
An aliquot of inhibitor was added to a solution of enzyme and aliquots removed with time and assayed for remaining activity.
[b]Inhibitor concentrations were from 0.01 to 0.51 mM.
[c]Inhibitor concentrations were from 0.001 to 0.18 mM.
[d]Inhibitor concentrations were from 0.004 to 0.33 mM.
[e]Inhibitor concentrations were from 0.002 to 0.35 mM.
[f]Inhibition was not time dependent, 81% inhibition was obtained at 0.49 mM.
[g]Inhibition was not time dependent, 87% inhibition was obtained at 47 μM.
[h]No inhibition.
[i]Inhibition was not time dependent, 87% inhibition was obtained at 0.53 mM.

TABLE V

Inactivation Rates for Inhibition of Chymases by Substituted Isocoumarins[a].

| | $k_{obs}/[I]$ (M$^{-1}$s$^{-1}$) | | |
|---|---|---|---|
| Inhibitors | Rat Mast Cell Protease II[b] | Human Skin Chymase[c] | Human Lung Chymase[d] |
| 7-guanidino-3-ethoxy-4-chloroisocoumarin | 1100 | 33 | 540 |
| 7-guanidino-3-(2-phenyl-ethoxy)-4-chloro-isocoumarin | 4100 | 22 | — |

[a]Inactivation rates were measured at 0.1 M Hepes, 0.5 M NaCl, pH 7.5, 8–12% Me$_2$SO and 25° C. by incubation method. An aliquot of inhibitor was added to a solution of enzyme and aliquots were removed with time and assayed for the remaining activity.
[b]Inhibitor concentration were from 0.007 mM to 0.013 mM.
[c]Inhibitor concentration were from 0.41 mM to 0.53 mM.
[d]Inhibitor concentration was 0.38 mM.

TABLE VI

Inactivation of Human Plasmin and Recombinant Human Tissue Plasminogen Activator by Substituted Isocoumarins[a].

| Inhibitor | $k_{obs}/[I]$ (M$^{-1}$s$^{-1}$) | |
|---|---|---|
| | Plasmin[b] | Plasminogen Activator[c] |
| 3,4-dichloroisocoumarin | | 73 |
| 3-(3-aminopropoxy)isocoumarin | 36 | |
| 3-(3-aminopropoxy)-4-chloroisocoumarin | 770 | 10 94 |
| 3-(3-isothiureidopropoxy)-4-chloro-isocoumarin | | 4,690 |
| 7-amino-3-(3-isothiureido-propoxy)-4-chloroisocoumarin | 4,340 | 5,690 |
| 7-guanidino-3-methoxyisocoumarin | 320 | |
| 7-guanidino-3-methoxy-4-chloro-isocoumarin | 3,500 | 4,420 |
| 7-guanidino-3-ethoxy-4-chloro-isocoumarin | 12,320 | 7,720 |
| 7-guanidino-3-(2-phenylethoxy)-4-chloro-isocoumarin | 4,140 | 6,780 |
| 7-(glycylamino)-3-methoxy-4-chloro-isocoumarin | 1,470 | |
| 7-(alanylamino)-3-methoxy-4-chloro-isocoumarin | 31 | |

TABLE VI-continued

Inactivation of Human Plasmin and Recombinant Human Tissue Plasminogen Activator by Substituted Isocoumarins[a].

| Inhibitor | $k_{obs}/[I]$ (M$^{-1}$s$^{-1}$) | |
|---|---|---|
| | Plasmin[b] | Plasminogen Activator[c] |
| isocoumarin | | |

[a]Inactivation constants were measured at 0.1 M Hepes, 0.5 M NaCl (or 0.01 M CaCl$_2$), pH 7.5, 8–12% Me$_2$SO and 25° C.
[b]Inhibitor concentrations were from 4 μM to 330 μM.
[c]Inhibitor concentrations were from 7 μM to 44 μM.

TABLE VII

Inactviation Rates of Mouse Granzyme A, Human Granzyme A and Q-13 Tryptase by Substituted Isocoumarins[a].

| Inhibitors | $k_{obs}/[I]$(M$^{-1}$s$^{-1}$) | | |
|---|---|---|---|
| | Mouse Granzyme A[b] | Human Granzyme A[b] | Human Q-31 Tryptase[c] |
| 3,4-dichloroisocoumarin | 50 | 50 | 29/ |
| 3-(3-aminopropoxy)-4-chloro-isocoumarin | 770 | 2,010 | |
| 3-(3-isothiureido-propoxy)-4-chloro-isocoumarin | 17,500 | 18,420 | 12,830 |
| 7-amino-3-(3-isothiureido-propoxy)-4-chloro-isocoumarin | 3,000 | 6,750 | 1,960 |
| 7-guanidino-3-methoxy-4-chloro-isocoumarin | 15,000 | | 6,620 |
| 7-guanidino-3-ethoxy-4-chloro-isocoumarin | 26,200 | 6,850 | 6,180 |
| 7-guanidino-3-(2-phenylethoxy)-4-chloro- | 6,400 | | 1,880 |

TABLE VII-continued

Inactivation Rates of Mouse Granzyme A, Human Granzyme A and Q-13 Tryptase by Substituted Isocoumarins[a].

| Inhibitors | $k_{obs}/[I](M^{-1}s^{-1})$ | | |
|---|---|---|---|
| | Mouse Granzyme A[b] | Human Granzyme A[b] | Human Q-31 Tryptase[c] |
| isocoumarin | | | |

[a]Inactivation rates were measured at 0.1 M Hepes, 0.01 M CaCl₂, pH 7.5, 8% Me₂SO and 25° C. by incubation method. Z-Arg-SBzl (74–85 μM) was used as the substrate to monitor the residual enzymatic activity.
[b]Inhibitor concentrations were from 0.4 μM to 45 μM.
[c]Inhibitor concentrations were from 3 μM to 500 μM.

TABLE VIII

Half-Lives for Spontaneous Hydrolysis of Isocoumarin Derivatives in Hepes Buffer[a], Human Plasma and Rabbit Plasma.

| Compounds | t½ (min) | | |
|---|---|---|---|
| | Hepes Buffer | Human Plasma | Rabbit Plasma |
| 3-(3-aminopropoxy)isocoumarin | 606 | | |
| 3-(3-aminoprpoxy)-4-chlorosisocoumarin | 123 | | |
| 3-(2-isothiureidoethoxy)-4-chloro isocoumarin | 83 | | |
| 3-(3-isothiureidopropoxy)-4-chloro-isocoumarin | 99 | 0.5 | |
| 7-amino-3-(3-isothiureidopropoxy)-4-chloroisocoumarin | 90 | 165 | 140 |
| 7-guanidino-3-methoxyisocoumarin | 252 | | |
| 7-guanidino-3-methoxy-4-chloroisocoumarin | 44 | 6.7 | |
| 7-guanidino-3-ethoxyisocoumarin | 136 | | |
| 7-guanidino-3-ethoxy-4-chloroisocoumarin | 39 | 8.2 | 4.2 |
| 7-guanidino-3-(2-phenylethoxy) isocoumarin | 140 | | |
| 7-guanidino-3-(2-phenylethoxy)-4-chloro-isocoumarin | 36 | 4.5 | |

[a]Conditions were 0.1 Hepes, 0.5 M NaCl, pH 7.5 and 9% Me₂SO at 25° C. Spontaneous hydrolysis rates were measured spectrophotometrically by monitoring the decrease in absorbance due to the isocoumarin ring system (wavelength 335–380 nm) using the first-order rate law.

TABLE IX

Effect of Substituted Isocoumarins on PT and APTT of Human and Rabbit Plasma.

| Compounds | [I] (μM) | Human Plasma | | Rabbit Plasma | |
|---|---|---|---|---|---|
| | | PT (sec) | APTT (sec) | PT (sec) | APTT (sec) |
| Control | 0 | 12.6 | 26.7 | 12.3[a] | 19.0 |
| | | | | 14.3[b] | |
| 3,4-dichloroisocoumarin | 33 | 12.4 | 26.6 | | |
| | 45 | | 26.0 | | |
| 7-guanidino-3-methoxy-4-chloro-isocoumarin | 21 | 16.5 | 83.8 | | |
| 7-guanidino-3-ethoxy-4-chloro-isocoumarin | 4.3 | | 74.8 | | |
| | 15 | | | 14.2[a] | |
| | 21 | 22.4 | >120 | | |
| | 31 | | | 27.4[a] | 60.5 |
| | | | | 17.2[b] | |
| | 53 | 31.4 | >120 | | |
| | 75 | 44.2 | | | |
| | 107 | 80 | >120 | | |
| | 124 | | | >120[b] | |
| 7-guanidino-3-(2-phenyl-ethoxy)-4-chloroisocoumarin | 27 | 13.0 | 57.3 | | |
| 3-(3-isothiureidopropoxy)-4-chloro-isocoumarin | 31 | 12.3 | 25.8 | | |
| 7-amino-3-(3-isothiureidopropoxy)-4-chloro-isocoumarin | 2.9 | | 100.8 | | |
| | 29 | 19.4 | >120 | | |
| | 33 | | | 13.7[a] | 68.6 |

TABLE IX-continued

Effect of Substituted Isocoumarins on PT and APTT of Human and Rabbit Plasma.

| Compounds | [I] (μM) | Human Plasma | | Rabbit Plasma | |
|---|---|---|---|---|---|
| | | PT (sec) | APTT (sec) | PT (sec) | APTT (sec) |
| | 131 | | 62.0[a] | | |

[a]Plasma and inhibitor were incubated at 37° C. for 1 min., Dade thromboplastin reagent was then added.
[b]Plasma and inhibitor were incubated at 37° C. for 3 min., Orthobrain thromboplastin reagent was then added.

TABLE X

The in vivo effect of 7-amino-4-chloro-3-(3-isothiureidopropoxy)isocoumarin on APTT with continuous infusion to rabbits.

| Dose (mg/ml) | APTT (sec) | | |
|---|---|---|---|
| | at 0 min (pre-infusion) | at 10 min (during infusion) | at 25 min (post-infusion) |
| 0.4 | 19.0 | 35.5 | 19.8 |
| 0.6 | 21.1 | 44.5 | 22.6 |
| 0.8 | 19.4 | 49.9 | 18.6 |
| 1.0 | 21.0 | 58.5 | 17.6 |
| 1.2 | 21.0 | 72.1 | 25.5 |

TABLE XI

The in vivo effect of 7-amino-4-chloro-3-(3-isothiureidopropoxy)isocoumarin on APTT and ACT with a uz,2/31 continuous infusion of 0.8 mg/ml to rabbits for 17 min.

| Time (min) | APTT (sec) | ACT (sec) |
|---|---|---|
| 0 | 19.2 | 175 |
| 5 | 29.9 | 197 |
| 10 | 43.4 | 265 |
| 16 | 44.4 | 247 |
| 22 | 18.1 | 175 |
| 29 | 18.1 | 165 |
| 32 | 16.8 | 168 |
| 37 | 17.4 | 180 |

What is claimed is:

1. A method of inhibiting blood clotting of mammalian blood comprising contacting said blood with a therapeutically amount of a compound having the following structure:

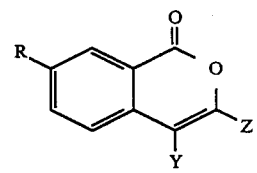

or a pharmaceutically acceptable salt thereof, wherein
R is selected from the group consisting of —NH—C(=NH)NH₂, —C(=NH)NH₂, amino-C₁₋₆ alkyl, and isothiureido-C₁₋₆ alkyl,
Z is selected from the group consisting of H, halogen, C₁₋₆ alkyl, C₁₋₆ alkyl with a phenyl group attached to the alkyl group, C₁₋₆ fluorinated alkyl, C₁₋₆ alkyl with a hydroxyl group attached to the alkyl group, C₁₋₆ alkyl with a C₁₋₆ alkoxy group attached to the alkyl group, C₁₋₆ alkoxy, C₁₋₆ fluorinated alkoxy, C₁₋₆ alkoxy with a phenyl group attached to the alkoxy group, benzyloxy group wherein the phenyl group is unsubstituted or substituted by one or two substituents selected from halogen, trifluoromethyl, NO₂, cyano, methyl, methoxy, acetyl, carboxyl, OH, and amino, and Y is selected from the group consisting of H, halogen, trifluoromethyl, methyl, OH, and methoxy.

2. A method of inhibiting clotting of mammalian blood comprising contacting said blood with a therapeutically effective amount of a compound having the following structure:

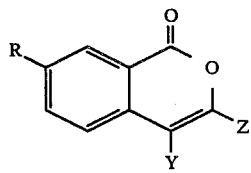

or a pharmaceutically acceptable salt thereof, wherein

Z is selected from the group consisting of $C_{1-6}$ alkoxy with an amino group attached to the alkoxy group, $C_{1-6}$ alkoxy with an isothiureido group attached to the alkoxy group, $C_{1-6}$ alkoxy with a guanidino group attached to the alkoxy group, $C_{1-6}$ alkoxy with an amidino group attached to the alkoxy group, $C_{1-6}$ alkyl with an amino group attached to the alkyl group, $C_{1-6}$ alkyl with an isothiureido group attached to the alkyl group, $C_{1-6}$ alkyl with a guanidino group attached to the alkyl group, $C_{1-6}$ alkyl with an amidino group attached to the alkyl group, R is selected from the group consisting of H, OH, NH₂, NO₂ halogen, $C_{1-6}$ alkoxy, $C_{1-6}$ fluorinated alkoxy, $C_{1-6}$ alkyl, amino-$C_{1-6}$ alkyl, M—AA—NH—, M—AA—O—, wherein AA represents alanine, valine, leucine, isoleucin, proline, methionine, phenylalanine, tryptophan, glycine, serine, threonine, cysteine, tyrosine, asparagine, glutamine, aspartic acid, glutamic acid, lysine, arginine, histidine, beta-alanine, beta-alanine, norleucine, norvaline, alpha-aminobutyric and epsilon-aminocaproic acid, citrulline, hydroxyproline, ornithine and sarcosine, wherein M represents H, lower alkanoyl having 1 to 6 carbons, carboxyalkanoyl, hydroxyalkanoyl, amino-alkanoyl, benzene sulfonyl, tosyl, benzoyl, and lower alkyl sulfonyl having 1 to 6 carbons, and Y is selected from the group consisting of H, halogen, trifluoromethyl, methyl, OH and methoxy.

3. A method of inhibiting clotting of mammalian blood comprising contacting said blood with a therapeutically effective amount of a compound having the following structure:

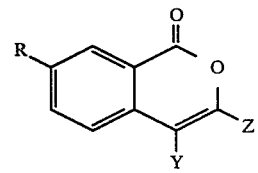

or a pharmaceutically acceptable salt thereof, wherein

R is selected from the group consisting of —NH—C(=NH)NH₂, —C(=NH)NH₂, amino-$C_{1-6}$ alkyl, isothiureido-$C_{1-6}$ alkyl, Z is selected from the group consisting of $C_{1-6}$ alkoxy with an amino group attached to the alkoxy group, $C_{1-6}$ alkoxy with an isothiureido group attached to the alkoxy group, $C_{1-6}$ alkoxy with a guanidino group attached to the alkoxy group, $C_{1-6}$ alkoxy with an amidino group attached to the alkoxy group, $C_{1-6}$ alkyl with an amino group attached to the alkyl group, $C_{1-6}$ alkyl with an isothiureido group attached to the alkyl group, $C_{1-6}$ alkyl with a guanidino group attached to the alkyl group, $C_{1-6}$ alkyl with an amidino group attached to the alkyl group, and Y is selected from the group consisting of H, halogen, trifluoromethyl, methyl, OH and methoxy.

4. The method of claim 1 wherein said blood is circulating within the body of the subject.

5. The method of claim 2 wherein said blood is circulating within the body of the subject.

6. The method of claim 3 wherein said blood is circulating within the body of the subject.

7. The method of claim 1 wherein said blood is circulating outside the body of the subject.

8. The method of claim 2 wherein said blood is circulating outside the body of the subject.

9. The method of claim 3 wherein said blood is circulating outside the body of the subject.

* * * * *